United States Patent
Cao et al.

(10) Patent No.: US 9,498,554 B2
(45) Date of Patent: Nov. 22, 2016

(54) DISPENSING DEVICE

(75) Inventors: Hai Yan Cao, Shanghai (CN); Amos Chen, Pudong District (CN); Shumao Han, Shanghai (CN); Joanna Jia, PuDong (CN); Salvador S. Munoz, Grayslake, IL (US); Deliang Shi, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 858 days.

(21) Appl. No.: 13/556,977

(22) Filed: Jul. 24, 2012

(65) Prior Publication Data

US 2014/0027530 A1 Jan. 30, 2014

(51) Int. Cl.
 *A61L 9/04* (2006.01)
 *A61L 9/12* (2006.01)
 *A01M 1/20* (2006.01)

(52) U.S. Cl.
 CPC .............. *A61L 9/042* (2013.01); *A01M 1/2044* (2013.01); *A01M 1/2055* (2013.01); *A61L 9/12* (2013.01); *A61L 2209/131* (2013.01)

(58) Field of Classification Search
 CPC ........... A61L 9/04; A61L 9/042; A61L 9/12; A61L 9/127; A01M 1/2022; A01M 1/2027; A01M 1/2044; A01M 1/2055
 See application file for complete search history.

(56) References Cited

U.S. PATENT DOCUMENTS

| 3,116,077 | A | 12/1963 | Bird |
| 4,228,614 | A | 10/1980 | Cardarelli |
| 4,484,768 | A | 11/1984 | Norfleet |
| 4,802,626 | A | 2/1989 | Forbes et al. |
| 5,516,504 | A | 5/1996 | Tominson |
| 6,171,608 | B1 | 1/2001 | Schmitt et al. |
| 6,327,813 | B1 | 12/2001 | Ishiwatari |
| 6,360,447 | B1 | 3/2002 | Foley |
| 6,360,477 | B1 | 3/2002 | Flashinski et al. |
| 6,520,365 | B2 | 2/2003 | Schneider |
| 6,534,079 | B1 | 3/2003 | Munagavalasa |
| 6,551,560 | B1 | 4/2003 | Flashinski et al. |
| 6,599,525 | B2 | 7/2003 | Scamilla Aledo et al. |
| 6,616,004 | B1 | 9/2003 | Erickson et al. |
| 6,631,891 | B1 | 10/2003 | Slade |
| 6,736,285 | B2 | 5/2004 | Stewart-Stand |
| 6,755,453 | B2 | 6/2004 | Kellas |
| 6,909,840 | B2 | 6/2005 | Harwig et al. |
| 6,913,733 | B2 | 7/2005 | Hardy et al. |
| 6,976,729 | B2 | 12/2005 | Kellas |

(Continued)

FOREIGN PATENT DOCUMENTS

| CN | 101116439 | 2/2008 |
| EP | 1328464 B1 | 7/2003 |

(Continued)

OTHER PUBLICATIONS

PCT/US2013/051775 International Search Report and Written Opinion dated Jan. 14, 2014.

(Continued)

*Primary Examiner* — Darren W Gorman (57) ABSTRACT

A dispensing device for release of an air treatment material includes a semi-permeable substrate having a mesh size between about 15 strands per cm to about 79 strands per cm and a support component for supporting the semi-permeable substrate. The dispensing device releases the air treatment material at a rate of at least about 0.05 mg/hr at about 25° C.

20 Claims, 6 Drawing Sheets (56) References Cited

U.S. PATENT DOCUMENTS

| | | | |
|---|---|---|---|
| 7,017,829 B2 | 3/2006 | Martens, III et al. |
| 7,051,949 B2 | 5/2006 | Aiyama |
| 7,152,809 B2 | 12/2006 | Ketcha et al. |
| 7,188,780 B2 | 3/2007 | Martens, III |
| 7,213,770 B2 | 5/2007 | Martens, III et al. |
| 7,344,729 B2 | 3/2008 | Kemmis et al. |
| 7,360,671 B2 | 4/2008 | Slade |
| 7,398,013 B2 | 7/2008 | He et al. |
| 7,426,799 B2 | 9/2008 | Christianson et al. |
| 7,503,675 B2 | 3/2009 | Demarest et al. |
| 7,544,332 B2 | 6/2009 | De Silva et al. |
| 7,581,558 B2 | 9/2009 | Martin et al. |
| 7,887,759 B2 | 2/2011 | Triplett |
| 7,887,826 B2 | 2/2011 | Costa |
| 8,047,837 B2 | 11/2011 | Furner et al. |
| 8,070,006 B2 | 12/2011 | Austin et al. |
| 8,091,741 B2 | 1/2012 | Pritchard |
| 8,093,444 B2 | 1/2012 | Flick |
| 2003/0060350 A1 | 3/2003 | Taylor et al. |
| 2003/0168520 A1 | 9/2003 | Triplett et al. |
| 2003/0199421 A1 | 10/2003 | Copfer |
| 2005/0132500 A1 | 6/2005 | Karl et al. |
| 2005/0284866 A1 | 12/2005 | Oakner et al. |
| 2008/0265053 A1 | 10/2008 | Guzman |
| 2010/0055075 A1 | 3/2010 | Marsala et al. |
| 2010/0236709 A1 | 9/2010 | Mutch |
| 2011/0010817 A1 | 1/2011 | Théberge et al. |
| 2011/0117156 A1 | 5/2011 | Lin et al. |
| 2011/0198808 A1 | 8/2011 | Fischer et al. |
| 2011/0305644 A1 | 12/2011 | Vijay et al. |
| 2012/0055075 A1 | 3/2012 | Winkler et al. |

FOREIGN PATENT DOCUMENTS

| | | |
|---|---|---|
| EP | 1182932 B1 | 8/2003 |
| EP | 1526770 | 5/2005 |
| EP | 1661458 A1 | 5/2006 |
| GB | 2380940 | 4/2003 |
| GB | 2407770 | 5/2005 |
| GB | 2407771 | 5/2005 |
| GB | 2417902 | 3/2006 |
| GB | 2421184 A | 6/2006 |
| JP | 2000189032 A | 7/2000 |
| JP | 2005298362 | 10/2005 |
| JP | 4182512 B2 | 11/2008 |
| JP | 2014-058455 A | 4/2014 |
| WO | 02083043 A1 | 8/2002 |
| WO | 03032723 A1 | 4/2003 |
| WO | 2004096588 A2 | 11/2004 |
| WO | 2005044001 | 5/2005 |
| WO | 2005044320 A1 | 5/2005 |
| WO | 2005046332 | 5/2005 |
| WO | 2006002395 A2 | 1/2006 |
| WO | 2006088139 | 2/2006 |
| WO | 2006044382 A2 | 4/2006 |
| WO | 2006134353 | 6/2006 |
| WO | 2007062471 A1 | 6/2007 |
| WO | 2008012507 | 1/2008 |
| WO | 2011030122 | 3/2011 |
| WO | WO2012032310 A1 | 3/2012 |

OTHER PUBLICATIONS

Fire Electricity Safety Essential )Oil Baby Children Repellent Paper Mosquito Coil Killer, website, Mar. 4, 2013, 6 pages, Zhejiang China, http://www.aliexpress.com/store/product/Free-Shipping-Wholesales-50PCS-LOT-NO-Fire-Electricity-safety-Essential-oil-Baby-children-Repellent-Paper-Mosquito/610329_567352609.html.

Argueta, Kawada, and Takagi, "Spatial repellency of metofluthrin-impregnated multilayer paper strip against Aedes albopictus under outdoor conditions, Nagasaki, Japan", Jun. 28, 2004, 6 pages, vol. 55, No. 3.

FIG. 7

DISPENSING DEVICE

CROSS REFERENCE TO RELATED APPLICATIONS

None.

REFERENCE REGARDING FEDERALLY SPONSORED RESEARCH OR DEVELOPMENT

Not applicable.

SEQUENTIAL LISTING

Not applicable.

BACKGROUND OF THE DISCLOSURE

1. Field of the Disclosure

The present disclosure relates to a dispensing device having a substrate supported by a support member, and in particular, to a dispensing device having a substrate angled with respect to the support member to promote air flow thererthrough.

2. Description of the Background of the Disclosure

Various volatile material dispensing devices are known in the prior art that generally comprise a reservoir that holds a volatile material and optionally includes a housing or support structure to retain the reservoir. The prior art dispensing devices typically either allow passive diffusion of the volatile material to occur without the aid of a dispensing mechanism or enhance and/or facilitate the release of the volatile material using a dispensing mechanism. Typical dispensing mechanisms used in volatile material dispensing devices include a heating device and/or a fan that either heats and/or supplies air, respectively.

Many passive dispensing devices of the prior art utilize a solid or semi-solid block of material or a volatile material laden gel disposed within a housing. In particular, one prior art dispensing device comprises a container having a candle therein. When lit, the candle emits a volatile material. Another prior art dispensing device uses a conical gel shaped surface impregnated with a volatile material. The conical gel surface is disposed within a housing having an adjustable cap. The cap may be adjusted upwardly or downwardly to expose the surface area of the conical gel surface to varying degrees. In a different prior art diffusion device, the diffusion device uses a reservoir having a semi-permeable film disposed thereon and a volatile material disposed within the reservoir. The volatile material diffuses out of the reservoir through the semi-permeable membrane. Another prior art diffusion device includes a substantially flat substrate having a volatile material thereon. The volatile material is slowly released into the surrounding atmosphere.

One draw-back of some of the aforementioned prior art devices is that the devices are typically not designed to be hung from a surface, such as a wall or ceiling. Prior art devices that are hung on the wall are usually automatically operated to dispense the volatile material at set intervals or based on a particular condition, such as with the use of a sensor, so that the user does not have to physically touch or interact with the device to effect dispensing. Such electrical requirements make the devices more complex and expensive to manufacture and sell. Further, such devices are more complicated for users to operate.

A further drawback of some of the prior art device, such as those that require user interaction to hang, is that a user must touch the substrate that is impregnated with the volatile material. Therefore, it is desirable to position a dispensing device in an operable position without touching the substrate or portions of the dispensing device that contain a volatile material, such as an insecticide. It is further desirable to locate such diffusion devices out of the reach of children when the dispensing device is in use.

Finally, dispensing devices that have solid or substantially solid substrates typically do not allow either any air, or a sufficient amount of air, to flow therethrough to aid in dispersing the volatile material over a broad area. Insufficient airflow is further exacerbated when a solid or semi-solid substrate of a dispensing device is disposed adjacent a wall or ceiling.

Therefore, it would be desirable to have a three-dimensional dispensing device specifically designed to be hung on a surface such as a wall or a ceiling that is operable without human intervention or electronic parts (including sensors and motors). It would further be further desirable to have a dispensing device that is designed to allow sufficient airflow therethrough, even when the dispensing device is disposed adjacent a vertical surface. Finally, it would be desirable to provide a low-cost dispensing device that is positioned into an operable position without human interaction with a volatile material. The present disclosure provides new and non-obvious dispensing devices, which address one or more of the above issues.

SUMMARY OF THE INVENTION

According to one aspect of the invention, a dispensing device for release of an air treatment material includes a semi-permeable substrate having a mesh size between about 15 strands per cm to about 79 strands per cm and a support component for supporting the semi-permeable substrate. The dispensing device releases the air treatment material at a rate of at least about 0.05 mg/hr at about 25° C.

According to another aspect of the invention, a dispensing device for release of an air treatment material comprises a substrate and a support component that supports the substrate. The substrate comprises two wing portions extending outwardly from the support component. The two wing portions form an angle of between about 90 degrees to about 180 degrees with respect to each other to promote air flow through the dispensing device.

According to a different aspect of the invention, a method of positioning a dispensing device in an operative position comprises the steps of providing a substrate within a container, wherein the substrate includes two wing portions that are adjacent one another and have an elastic material attached thereto. The method further includes the step of opening the container and removing the substrate, whereby the elastic material acts to open the two wings of the substrate into an operable position and the wings are disposed at an angle of between about 90 degrees to about 180 degrees with respect to each other in the operable position.

DETAILED DESCRIPTION OF THE DRAWINGS

As depicted in FIGS. 1-7, a dispensing device 100 generally includes a substrate 102 that is supported by a reinforced support component 104. An air treatment chemical 106 (see FIG. 2) is disposed on the substrate 102. The dispensing device 100 is adapted to passively dispense the air treatment chemical 106 when air flows through and/or around the substrate 102.

Figure 1:
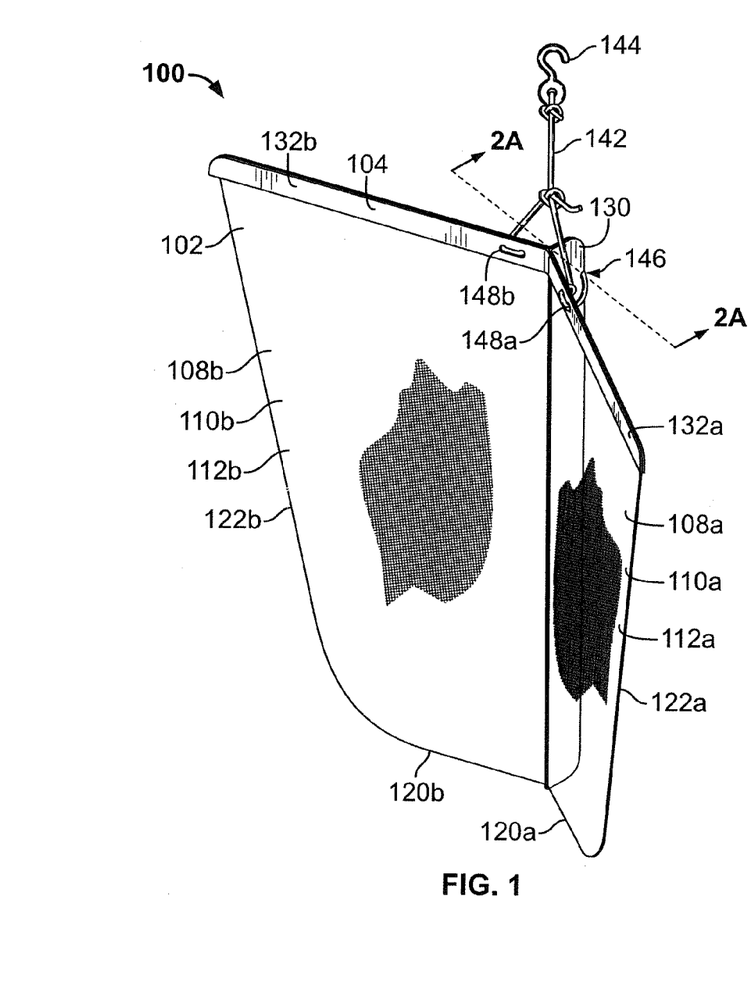
FIG. 1 is a front isometric view of a first embodiment of a dispensing device having a substrate and a support component.
Figure 4:
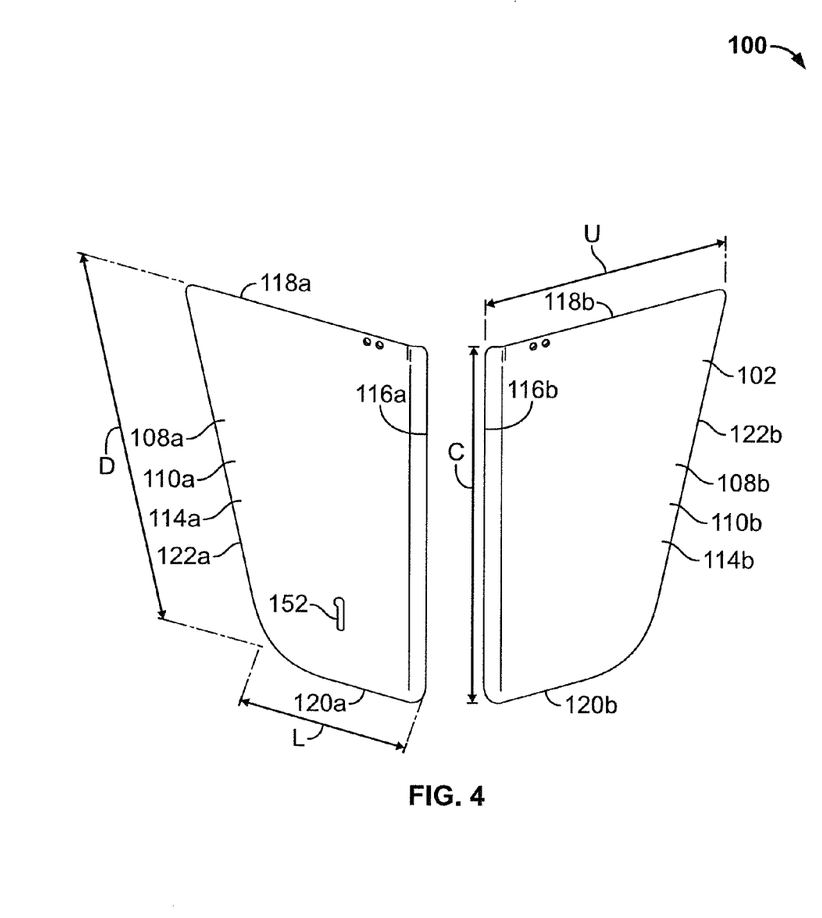
FIG. 4 is an rear isometric view of the substrate of FIG. 1.

Still referring to FIG. 1, the substrate 102 comprises a plurality of wing portions 108a, 108b that extend outwardly from the support component 104. Each wing portion 108a, 108b includes a substantially flat surface 110a, 110b defined by an interior surface 112a, 112b and an exterior surface 114a, 114b. As best seen in FIG. 4, each wing 108a, 108b comprises four sides and includes a central support edge 116a, 116b, an upper edge 118a, 118b, a lower edge 120a, 120b, and an outer edge 122a, 122b, respectively.

Figure 1A:
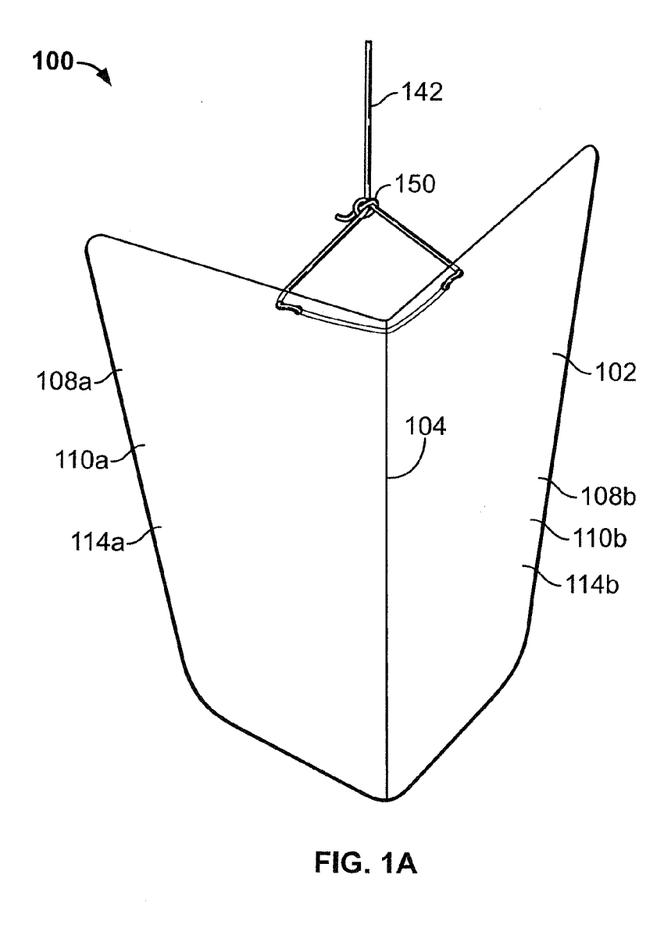
FIG. 1A is a rear isometric view of a second embodiment of a dispensing device having a substrate comprising a single element.
Figure 2:
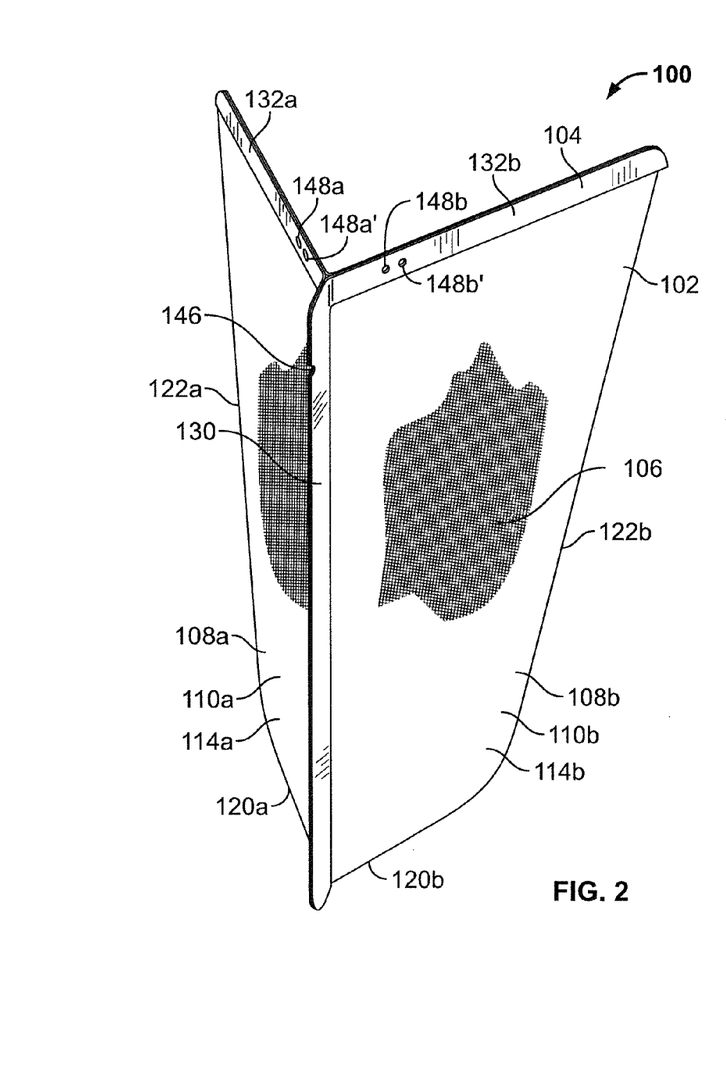
FIG. 2 is a rear isometric view of the dispensing device of FIG. 1.
Figure 2A:
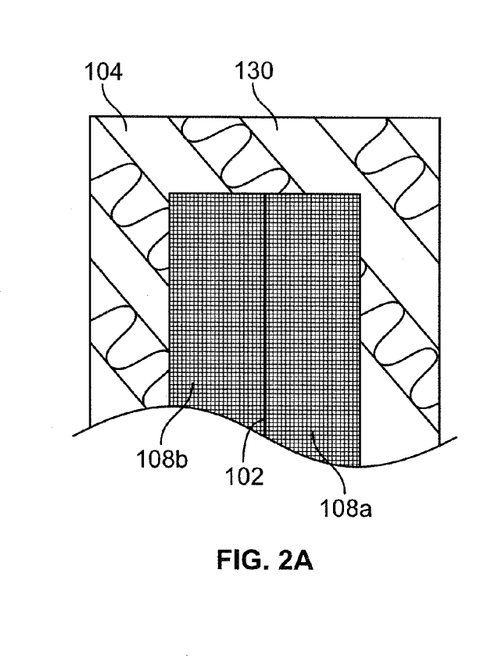
FIG. 2A is a cross-sectional view of the dispensing device of FIG. 1 taken along the line 2A-2A of FIG. 1.

The substrate 102 is designed to carry the air treatment material 106 thereon. In a preferred embodiment, the substrate 102 comprises a semi-permeable barrier defined by a plurality of connected strands. The connected strands are preferably flexible and crisscrossed to form a mesh web pattern and allow selective diffusion therethrough. In one embodiment, the substrate 102 comprises two separate elements that are held together via the support component 104 (see FIGS. 3 and 4). In a different embodiment, the substrate 102 comprises a single element that is folded or otherwise manipulated to provide a plurality of wing portions 108a, 108b (See FIG. 1A). One or more wing portions may extend from the support component 104.

By coating the substrate 102 with an appropriate air treatment chemical, air entering the device will acquire a portion of the volatile chemical, and dispense it from the dispensing device 100. Active release rates of at least 0.05 milligrams per hour (mg./hr.) or higher are preferred. Suitable actives are D-teflumethrin, transfluthrin, prallethrin, vaporthrin, metofluthrin, tefluthrin, and esbiothrin or other synthetic pyrethroids. The air treatment chemical may solely comprise an active, or for ease of handling the material may be dissolved in a hydrocarbon, alcohol, or other solvent. Alternatively, or in addition, the substrate 102 may also bear a fragrance, a deodorizer, or other air treatment chemical.

The substrate 102 is preferably capable of holding a dose of the active ingredient in a relatively even distribution thereon and also capable of allowing evaporation in response to the air flow. For an active ingredient that is hydrophobic and migrateable at common environmental temperatures between about 10° C. and 40° C. (e.g., D-teflumethrin), a suitable material includes, by way of example, nylon. The nylon may be characterized as having a basis weight ranging from 30 grams per square meter (gsm) to 150 grams per square meter (gsm) and may be fabricated from synthetic, natural, or combined synthetic and natural polymeric materials. In one preferred embodiment, the nylon is characterized by a thickness of between about 0.1 mm to about 0.8 mm, more preferably between about 0.2 mm to about 0.5 mm, and most preferably about 0.35 mm. The nylon is further characterized by a melting point of between about 150° C. to about 275° C., or between about 200° C. to about 250° C., or about 215° C. to about 225° C. The nylon has a mesh size of between about 5 strands per cm to about 80 strands per cm, between about 10 strands per cm to about 40 strands per cm, or most preferably about 16 strands per cm. In one embodiment, the nylon has a mesh size of between about 15 strands per cm to about 79 strands per cm.

The substrate 102 should also allow for wicking of the active ingredient following dosing to ensure efficient distribution throughout the substrate 102. Dosing may be accomplished by dropping, spraying, printing, or other conventional delivery of a liquid active ingredient on to the substrate 102. In one embodiment, the substrate 102 may be divided into a plurality of blocks for applying the active thereto. For example, the substrate 102 may be divided into 24 squares. In such a division, the active ingredient on each square centimeter comprises about 0.1 mg.

Turning again to FIGS. 3 and 4, each wing 108a, 108b of the substrate 102 is defined by a surface area that measures between about 50 $cm^2$ to about 500 $cm^2$, more preferably between about 125 $cm^2$ to about 225 $cm^2$, and most preferably about 175 $cm^2$. The total surface area of the substrate 102 is preferably between about 100 $cm^2$ to about 1000 $cm^2$, more preferably between about 300 $cm^2$ to about 500 $cm^2$, and most preferably between about 350 $cm^2$ to about 450 $cm^2$.

As best seen in FIG. 4, the central support edges 116a, 116b are defined by a length dimension C that is preferably between about 100 mm to about 300 mm, more preferably between about 180 mm to about 220 mm, and most preferably about 200 mm. The upper edges 118a, 118b are defined by a length dimension U that is preferably between about 50 mm to about 250 mm, more preferably between about 110 mm to about 150 mm, and most preferably about 135 mm. The lower edges 120a, 120b are defined by a length dimension L that is preferably between about 40 mm to about 120 mm, more preferably between about 60 mm to about 90 mm, and most preferably about 80 mm. The outer edges 122a, 122b are defined by a length dimension O that is preferably between about 100 mm to about 250 mm, more preferably between about 150 mm to about 200 mm, and most preferably about 180 mm. In one particular embodiment, the central support edges 116a, 116b include a length dimension C of about 200 mm, the upper edges 118a, 118b include a length dimension U of about 140 mm, the lower edges 120a, 120b include a length dimension L of about 80 mm, and the outer edges 122a, 122b include a length dimension O of about 180 mm.

Figure 5:
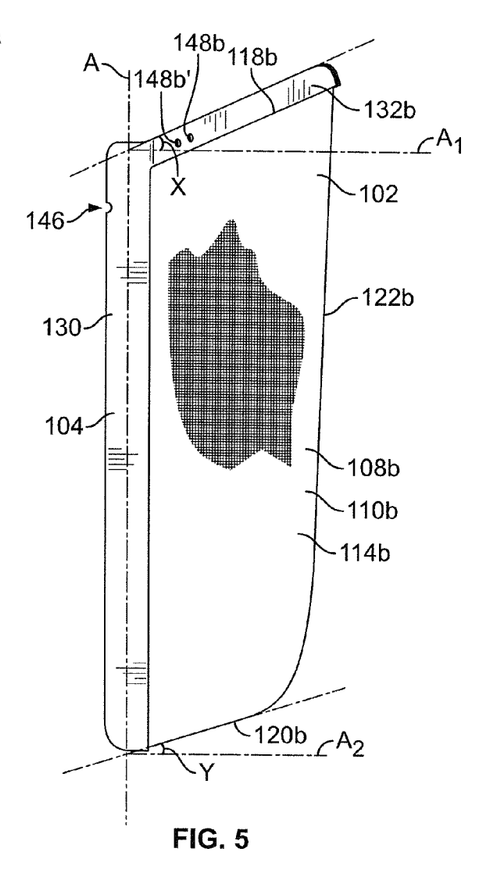
FIG. 5 is a side elevational view of the dispensing device of FIG. 1.
Figure 6:
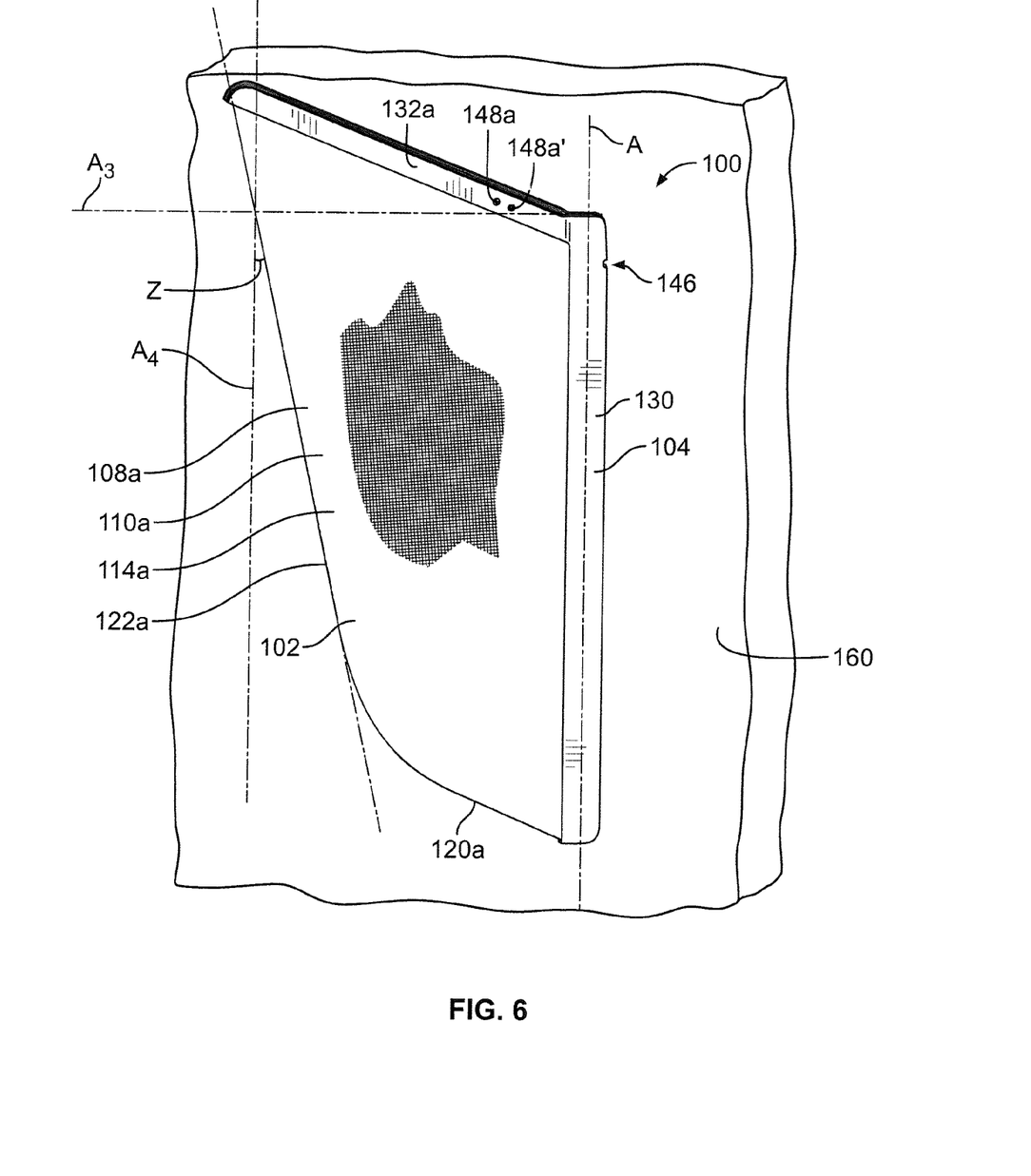
FIG. 6 is an isometric view of the dispensing device of FIG. 1 in a closed position within a container.

Now turning to FIG. 5, various portions of the substrate 102 are angled with respect to a central axis A that runs through the central support edges 116a, 116b and corresponding axes $A_1$ and $A_2$ that extend perpendicularly from the central axis A. In particular, the upper edges 118a, 118b each extend upwardly at an angle X between about 5 degrees to about 70 degrees, more preferably between about 10 degrees to about 50 degrees, and most preferably about 25 degrees, as measured with respect to axes A and $A_1$. Still referring to FIG. 5, the lower edges 120a, 120b each extend upwardly at an angle Y between about 5 degrees to about 70 degrees, more preferably between about 10 degrees to about 50 degrees, and most preferably about 20 degrees, as measured with respect to axes A and $A_2$. In one embodiment, the angle X and the angle Y of the upper edges 118a, 118b, and lower edges 120a, 120b, respectively, are the same. In a different embodiment, the angle X and the angle Y of the upper edges 118a, 118b, and lower edges 120a, 120b, respectively, are different from each other. As best seen in FIG. 6, the outer edges 122a, 122b are also angled with respect to an axis $A_3$ that is perpendicular to axis A and extends outwardly along an upper portion of the support component 104 and axis $A_4$, which extends perpendicularly from axis $A_3$. In particular, the outer edges 122a, 122b each extend at an angle Z of between about 5 degrees to about 50 degrees, more preferably between about 10 degrees to about 20 degrees, and most preferably about 15 degrees, as measured between the outer edges 122a, 122b and the axis $A_4$.

Again referring to FIG. 2, the support component 104 is adapted to provide support to the substrate 102 and comprises an elongate vertical portion 130 that terminates at two outwardly extending flange portions 132a, 132b. The support component 104 preferably provides some rigidity to the dispensing device 100 and assists in orienting the wings 108a, 108b, as will be described in more detail below. The vertical portion 130 further provides a gripping section for a user to handle the dispensing device 100 without touching the substrate 102. The support component 104 may comprise one integral element or may comprise a plurality of separate elements that are glued or otherwise joined together.

The substrate 102 and support component 104 may be configured with respect to each other in various manners. In one embodiment shown in FIG. 2A, the central edges 116a, 116b of each wing portion 108a, 108b are disposed within a recess within the vertical portion 130 of the support component 104. Similarly, the upper edges 118a, 118b of the wings 108a, 108b are disposed within a recess of each flange portion 132a, 132b of the support component 104. In a different embodiment, the substrate 102 is adhered or otherwise attached to an interior or exterior surface of the support component 104.

The support component 104 comprises a natural or synthetic fibrous material. In one embodiment, the support component 104 comprises paper, cardboard, paperboard, or the like. In a different embodiment, the support component 104 comprises a lower density polymer. In yet a different embodiment, the support component 104 comprises other polymer and/or polymer blends such as polypropylene, polyethylene, and/or polyethylene terephthalate. Suitable support materials 104 have a grammage of between about 100 g/m² to about 500 g/m², or between about 200 g/m² to about 400 g/m², or about 300 g/m². It is envisioned that the support component 104 may comprise other materials so long as the material is rigid enough to provide support to the substrate 102.

Figure 3:
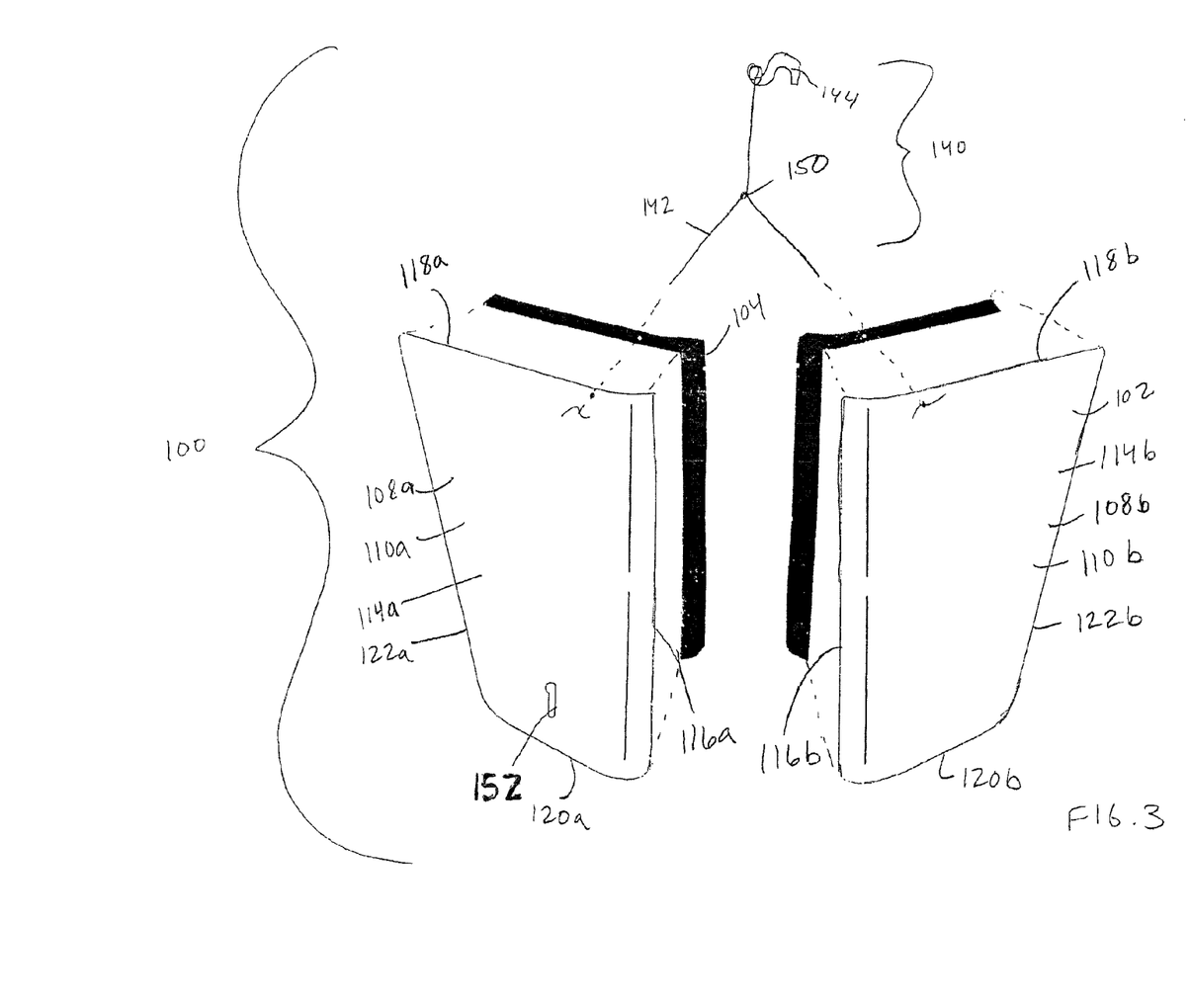
FIG. 3 is an exploded rear isometric view of the dispensing device of FIG. 1.

The support component 104 is further adapted to support a hanging assembly 140 (see FIGS. 1 and 3). The hanging assembly 140 comprises a string 142 and an attachment mechanism 144. As best seen in FIG. 1, the string 142 is attached to and extends through various portions of the dispensing device 100. In one embodiment, the string 142 extends through a slot 146 disposed along a back edge of the support component 104 and through openings 148a, 148b in the flange portion 132a, 132b of each wing 108a, 108b, respectively. The string 142 wraps back through adjacent openings 148a' and 148b' and upwardly away from the exterior surfaces 114a, 114b of each wing 108a, 108b until reaching a knotted portion 150. The string 142 extends upwardly from the knotted portion 150 in a substantially vertical manner before terminating at the attachment mechanism 144.

The string 142 is preferably elastic and comprises rope, twine, cord, yarn, or other like materials. The string 142 may be made from natural and/or synthetic materials such as cotton, wool, linen, silk, nylon, polyester, polyethylene, rayon, metal, or the like. The string 142 includes a diameter dimension of between about 1 mm to about 2.5 mm. In one embodiment, the string 142 is defined by a modulus of elasticity of between about $2 \times 10^5$ N/m² to about $8 \times 10^5$ N/m².

Figure 7:
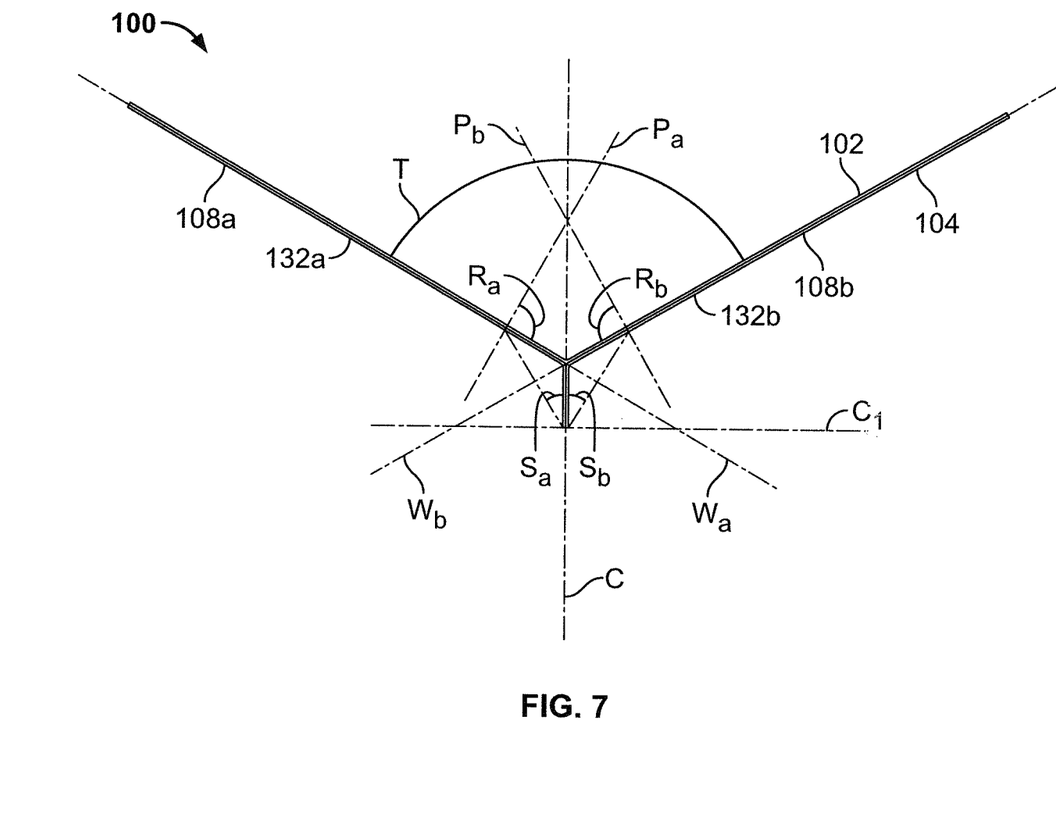
FIG. 7 is a top plan view of the dispensing device of FIG. 1 in an open position.

The string 142 is attached at various points to the dispensing device 100 in a manner that provides various benefits thereto. In particular, the string 142 forms various angles with respect to axes $W_a$ and $W_b$, defined by wings 108a, 108b and axes $P_a$ and $P_b$, which extend perpendicularly from axes $W_a$ and $W_b$, respectively. As depicted in FIG. 7, the string 142 forms an angle $R_a$ and $R_b$ with respect to the axes $W_a$ and $P_a$ and $W_b$ and $P_b$, respectively, that is between about 40 degrees to about 100 degrees, more preferably between about 70 degrees to about 95 degrees, and most preferably about 90 degrees. The string 142 also forms angles $S_a$ and $S_b$ with respect to the axes C and $C_1$, which extends perpendicularly from axis C. The angles $S_a$ and $S_b$ are between about 1 degree to about 45 degrees, more preferably between about 5 degrees to about 25 degrees, and most preferably about 10 degrees. Mounting the string 142 at these specific points ensures the dispensing device 100 remains in an open position at an angle that is beneficial to dispensing, as will be described in more detail hereinbelow.

The attachment mechanism 144 preferably allows the dispensing device 100 to be mounted, attached, or otherwise hung from a vertical or horizontal surface, such as, for example, a wall. In one embodiment, the attachment mechanism 144 comprises a hook. In a different embodiment, the attachment mechanism 144 comprises a suction cup. In yet a different embodiment, the attachment mechanism 144 comprises a looped end of the string 142 that allows the string 142 to be directly attached to a hook, wall, or other surface.

The dispensing device 100 optionally includes a use-up cue 152 (see FIG. 3) provided in the form of a useful life indicator that provides information about the extent of remaining life in the dispensing device 100. A suitable use-up cue is described in U.S. Pat. No. 7,892,483, owned by the same assignee as the present disclosure.

Now that the individual components have been discussed, the relationship thereto, and the operation of the dispensing device 100 will be discussed. Prior to use, the dispensing device 100 is preferably provided to a user in a sealed container 160 (See FIG. 6), such as a bag or other package. The sealed nature of the container 160 assists in retaining the chemical material 106 therein prior to use. The dispensing device 100 is disposed in a substantially flat orientation within the container 160, whereby interior surfaces 112a, 112b of the wings 108a, 108b are disposed adjacent each other. A folded orientation reduces the overall size of the container 160 needed to store the dispensing device 100. When a user desires to use the dispensing device 100, the user opens the container 160 and removes the dispensing device 100 therefrom. In a preferred embodiment, the user grasps the support member 104 to remove the dispensing device 100 without having to touch the substrate 102. The string 142 may be disposed within the slot 146 already, or the user may optionally insert the string 142 into the slot 146 to assist in opening the wings 108a, 108b thereby. Once the dispensing device 100 is removed from the container 160, the force of the string 142 disposed at angles disclosed herein, acts to open the wings 108a, 108b into an operable position (See FIG. 7).

The dispensing device 100 is capable of opening on its own into a fully operative position due to a variety of factors taken into consideration during the manufacturing of the dispensing device. In the present context, the phrase capable of opening on its own means that the dispensing device is able to move from a first position (substantially flat) into a second operative position (wings open to a specified angle) when outside barriers (i.e., the container) are removed. Such a configuration is desirable because it allows the user to set up the device without having to touch the substrate 102.

During the operational state, the dispensing device 100 is preferably hung from or otherwise supported by a surface such as a wall. In the operable position, the wings 108a, 108b of the dispensing device 100 are provided at a specified angle to enhance the air flow therearound. In particular, as best seen in FIG. 7, the wings 108a, 108b form an angle T with respect to each other of about 75 degrees to about 175 degrees, or more preferably about 90 degrees to about 180 degrees, or most preferably about 130 degrees.

In the operational state, the dispensing device 100 preferably has a release rate of the air treatment material 106 between about 0.01 to about 0.1 mg/hour, as measured at about 25° C. and an air flow of between about 0.01 to about 0.2 m/s. Although designed to be used with at least some airflow, the dispensing device 100 will still release at least some of the air treatment material with little or no airflow. In one particular embodiment, the dispensing device 100 has a release rate of between about 0.05 to about 0.08 mg/hr, at about 25° C. and an air flow of between about 0.01 to about 0.2 m/s.

The air treatment chemical disclosed in the embodiments herein may be a fragrance or insecticide disposed within a carrier liquid, a deodorizing liquid, or the like. The air treatment chemical may also comprise other actives, such as sanitizers, air fresheners, odor eliminators, mold or mildew inhibitors, insect repellents, and the like, or that have aromatherapeutic properties. The air treatment chemical alternatively comprises any volatile material known to those skilled in the art.

Any of the embodiments described herein may be modified to include any of the structures or methodologies disclosed in connection with different embodiments. Further, the present disclosure is not limited to substrate and/or support component shapes/sizes of the type specifically shown. Still further, the support component of any of the embodiments disclosed herein may be modified to work with various types of substrates consistent with the disclosure herein.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A dispensing device for release of an air treatment material, comprising:
    a semi-permeable substrate, the entire substrate having a mesh size between about 15 strands per cm to about 79 strands per cm, wherein the substrate holds an air treatment material;
    a support component for supporting the semi-permeable substrate, wherein the semi-permeable substrate extends from a peripheral edge of the support component; and
    a flange portion elongate about a single axis for supporting the semi-permeable substrate, wherein the semi-permeable substrate extends from a peripheral edge of the flange portion, and
    wherein the dispensing device releases the air treatment material at a rate of at least about 0.05 mg/hr at about 25° C.

2. The dispensing device of claim 1, wherein the semi-permeable substrate comprises nylon.

3. The dispensing device of claim 2, wherein the semi-permeable substrate has a surface area defined by a perimeter of the semi-permeable substrate that measures between about 300 cm$^2$ to about 500 cm$^2$.

4. The dispensing device of claim 1, wherein the semi-permeable substrate comprises two wings attached at the support component.

5. The dispensing device of claim 1, wherein the support component is defined by a grammage of between about 200 g/m$^2$ to about 400 g/m$^2$.

6. The dispensing device of claim 1, wherein the air treatment material is an insecticide.

7. The dispensing device of claim 6, wherein the air treatment material comprises teflumethrin, transfluthrin, prallethrin, vaporthrin, metofluthrin, tefluthrin, esbiothrin or other synthetic pyrethroids.

8. The dispensing device of claim 1, wherein the flange extends from a portion of the support component.

9. A dispensing device for release of an air treatment material, comprising:

a substrate; and a vertical support component and at least one outwardly extending flange portion that supports the substrate, wherein the substrate extends from a peripheral edge of the at least one outwardly extending flange portion, and wherein the substrate comprises two wing portions extending outwardly from the vertical support component, and wherein the two wing portions form an angle of between about 90 degrees to about 180 degrees with respect to each other to promote air flow through the dispensing device.

10. The dispensing device of claim 9, wherein the substrate comprises nylon.

11. The dispensing device of claim 9, wherein the substrate holds the air treatment material thereon and also allows migration of the air treatment material to allow evaporation thereof in response to air flow.

12. The dispensing device of claim 9, wherein each wing portion is angled with respect to a central axis defined by the support component.

13. The dispensing device of claim 12, wherein each wing portion includes an upper edge that extends upwardly at an angle between about 10 degrees to about 50 degrees as measured with respect to the central axis and a first axis extending perpendicularly therefrom.

14. The dispensing device of claim 13, wherein each wing portion includes a lower edge that extends upwardly at an angle between about 10 degrees to about 50 degrees as measured with respect to the central axis and a second axis extending perpendicularly therefrom.

15. The dispensing device of claim 14, wherein the angle of the upper edge and the angle of the lower edge about the central, first, and second axes, respectively, are substantially the same.

16. The dispensing device of claim 9 further including a hanging assembly having a string and an attachment mechanism.

17. The dispensing device of claim 16, wherein the string extends through the dispensing device and forms an angle of between about 70 degrees to about 90 degrees as measured from axes formed by the wings of the dispensing device and corresponding perpendicular axes extending therefrom.

18. The dispensing device of claim 9 further including a use-up cue.

19. The dispensing device of claim 9, wherein the air treatment material is an insecticide.

20. The dispensing device of claim 19, wherein the air treatment material comprises teflumethrin.

providing a substrate within a container, wherein the substrate includes two wing portions that are adjacent one another and having an elastic material attached thereto; and opening the container and removing the substrate, whereby the elastic material acts to open the two wings of the substrate into an operable position and the wings are disposed at an angle of between about 90 degrees to about 180 degrees with respect to each other in the operable position.

* * * * *